United States Patent [19]

Arai et al.

[11] Patent Number: 5,063,153

[45] Date of Patent: Nov. 5, 1991

[54] INTEGRAL MULTILAYER ANALYTICAL ELEMENT

[75] Inventors: Fuminori Arai; Takeshi Igarashi; Mitsutoshi Tanaka, all of Asaka, Japan

[73] Assignee: Fuji Photo Film Co., Ltd., Kanagawa, Japan

[21] Appl. No.: 107,674

[22] Filed: Oct. 9, 1987

[30] Foreign Application Priority Data

Oct. 9, 1986 [JP] Japan .................. 61-240288
Nov. 6, 1986 [JP] Japan .................. 61-265090
Nov. 6, 1986 [JP] Japan .................. 61-265091

[51] Int. Cl.$^5$ .................. C12Q 1/32; G01N 31/22
[52] U.S. Cl. .................. 435/26; 435/25; 435/188; 422/56; 422/57; 422/58; 427/2
[58] Field of Search .............. 422/56, 57, 58; 435/25, 435/26, 188; 427/2

[56] References Cited

U.S. PATENT DOCUMENTS

| 4,066,403 | 1/1978 | Bruschi .................. 23/230 |
| 4,273,870 | 6/1981 | Mollering et al. .................. 435/26 |
| 4,356,149 | 10/1982 | Kitajima et al. .................. 422/56 |
| 4,604,347 | 8/1986 | Arai et al. .................. 435/4 |
| 4,629,697 | 12/1986 | Limbach et al. .................. 435/26 |
| 4,781,890 | 11/1988 | Arai et al. .................. 422/56 |

FOREIGN PATENT DOCUMENTS 029104 5/1981 European Pat. Off. .
116361 2/1984 European Pat. Off. .
0182179 5/1986 European Pat. Off. .

OTHER PUBLICATIONS

Eastman Kodak Company, Potentiometric Methodologies Summary, Publication MP2-74; Nov. 1986, pp. 1-4.

Primary Examiner—Christine Nucker
Assistant Examiner—Laurie Scheiner
Attorney, Agent, or Firm—McAulay Fisher Nissen Goldberg & Kiel

[57] ABSTRACT

An improvement of a dry integral multilayer analytical element having functional layers which contain dehydrogenase, oxidized nicotinamide coenzyme, an electron transport compound and an electron acceptable dye-forming compound is disclosed. The improvement the analytical element resides in that an alkali agent or an alkaline buffer is contained in a layer which is different from a layer or layers containing the oxidized nicotinamide coenzyme and electron acceptable dye-forming compound.

8 Claims, No Drawings

INTEGRAL MULTILAYER ANALYTICAL ELEMENT

BACKGROUND OF THE INVENTION

1. Field of the Invention

The present invention relates to a dry integral multilayer analytical element containing an oxidized coenzyme and a process for the preparation of said element.

2. Description of Prior Art

Reactions in which dehydrogenase and a coenzyme are involved have been widely employed in clinical chemical analyses. For example, various reaction systems in which a dehydrogenase such as glycerol dehydrogenase, cholesterol dehydrogenase, lactate dehydrogenase, alcohol dehydrogenase, glutamate dehydrogenase, aldehyde dehydrogenase, $\alpha$-glycerophosphate dehydrogenase or glucose-6-phosphate dehydrogenase participates are employed for quantitative determination of substrate such as triglyceride, glycerol, cholesterol, lactic acid, glutamate, glycerol-3-phosphoric acid or glucose-6-phosphoric acid, and an enzyme such as aspartic acid aminotransferase (AST), lactate dehydrogenase (LDH), amylase or creatine kinase (CK). Through the reaction, quantitative analysis can be made by directly measuring increase or decrease of the amount of a reduced coenzyme. However, the conventionally employed NADH (i.e., nicotinamide adenine dinucleotide) or NADPH (i.e., nicotinamide adenine dinucleotide phosphate) has its maximum absorption peak at approx. 340 nm, and therefore the photometric measurement requires an expensive photometer for the measurement of a light in the ultraviolet region. Another drawback resides in that such measurement of a light in the ultraviolet region is easily influenced by a variety of coexisting compounds.

An alternative photometric analytical method using an electron acceptable dye-forming compound and an electron transmitter (i.e., carrier) in combination for forming a dye having an absorption peak in the visible ray region upon contact with the produced NADH was proposed for replacement of the above-described method of directly measuring the produced NADH (or NADPH). This method, however, has a problem that the reagent composition comprising the oxidized coenzyme, electron acceptable dye-forming compound and electron transmitter compound easily deteriorates to show lowering of reaction sensitivity when an analytical element containing such composition is stored for a long tiem of period. This problem is often observed particularly in the case that such composition is incorporated into a dry integrated multilayer analytical element as described in Japanese Patent Publication No. 53(1978)-21677 and Japanese Patent Provisional Publications No. 55(1980)-164356 and No. 60(1985)-222769.

Japanese Patent Provisional Publication No. 49(1974)-11395 proposes a multilayer analytical element in which the electron transporter compound among the above-mentioned three components is arranged in a different layer from the layer containing the remaining two components. Japanese Patent Provisional Publication No. 59(1984)-44658 discloses a method of dispersing a hydrophobic substance in a hydrophilic medium, whereby the electron transmitter does not substantially react with the dye-forming material. Further, Japanese Patent Provisional Publication No. 59(1984)-88096 proposes two methods, namely, a method of arranging the electron transporter compound and an electron acceptable dye precursor (i.e., electron acceptable dye-forming compound) in separate layers in the same manner as described in the above-mentioned Japanese Patent Provisional Publication No. 49(1974)-11395 and a method of arranging the two components in the same layer in the form of separate particles, so as that the two components do not substantially react with each other. However, in these cases (cases of separating the electron transporter component from the remaining two components), a reaction rate decreases because the progress of the reaction is predominantly defined by a diffusion speed of the separated reagents (particularly the electron transporter compound), and hence detection sensitivity is deteriorated.

It was found that when a composition for detecting the above-mentioned NADH (or NADPH) is used in a reagent layer of a dry integral multilaye analytical element (e.g., multilayer analytical elements for automatic chemical analysis as described in Japanese Patent Publication No. 53(1978)-21677, and Japanese Patent Provisional Publications No. 55(1980)-164356 and No. 60(1985)-222769), a dye-forming rate of the composition after storage at room temperature becomes less than $\frac{1}{2}$ of the initial speed within several weeks. It has been confirmed that the decrease of the speed is mainly caused by the deterioration of NAD coenzyme (or NADP coenzyme) not by the deterioration of the electron acceptable compound which is referred to in Japanese Patent Provisional Publication No. 57(1982)-132061. For preventing such deterioration of the coenzyme in a buffer solution, a measure of incorporating a chelating agent and an azide in combination is described in Japanese Patent Provisional Publication No. 59(1984)-82398. However, the use of the azide having explosion characteristics and toxicity is unfavorable from the viewpoints of safety and environmental pollution.

It is known that the reagent layer containing NAD coenzyme or NADP coenzyme preferably has a pH value in the vicinity of neutral level in all stages including a coating stage in order to avoid the deterioration of coenzyme in the storage. Also known is that diaphorase loses its activity when it is placed under a pH condition of less than approx. 6.0. On the other hand, it is known that the reaction system preferably has an alkaline pH value when dehydrogenase participates in the reaction. However, there has not been proposed any dry analytical element element simultaneously satisfying the above-mentioned conflict of the appropriate pH conditions.

SUMMARY OF THE INVENTION

Accordingly, an object of the present invention is to provide a dry multilayer analytical element containing dehydrogenase, an oxidized nicotinamide coenzyme, an electron transport compound (electron transmitter compound), and an electron acceptable dye-forming compound as reagent components, which shows a satisfactorily high analytical reaction rate without decrease of its analytical accuracy.

There is provided by the present invention an improvement of a dry multilayer analytical element comprising a light-transmissive, water-impermeable support and reagent layers provided on the support, the reagent layers containing dehydrogenase, oxidized nicotinamide coenzyme, an electron transport compound and an electron acceptable dye-forming compound wherein an alkali agent or an alkaline buffer is contained in a reagent layer which is different from a reagent layer containing said coenzyme and dye-forming compound.

According to the present invention, the oxidized nicotinamide coenzyme can be stably stored in the analytical element even under such conditions that the oxidized nicotinamide coenzyme, electron transporter compound and electron acceptable dye-forming compound are incorporated into one layer without separating these components from each other.

DETAILED DESCRIPTION OF THE INVENTION

The present invention can be applied to a variety of known dry analytical elements. Particularly, the invention is advantageously applied to an element comprising a liquid-permeable layer through which any of dehydrogenase, a reduced coenzyme-detecter composition and a liquid sample are permeable. The analytical element of the invention has at least two reagent layers provided on the support. The analytical element may contain other functional layers such as, a light-reflecting layer, a porous liquid spreading layer, a light-blocking layer, a filtration layer, a registration layer, a water-absorbing layer, and an undercoating layer. The reagent layer and other functional layer can be constituted to form a single layer. For instance, the porous spreading layer can contain a reagent or a reagent composition to form a reagent layer.

Various multilayer analytical elements are described in more detail, for example, in U.S. Pat. Nos. 3,992,158 and 4,042,335, and Japanese Patent Provisional Publications No. 51(1976)-40191, No. 55(1980)-164356 and No. 60(1985)-222769.

Preferred embodiments of constitution of the analytical elements are listed below.

(1) an element comprising two or more reagent layers arranged on the support;

(2) an element comprising a spreading layer serving as a reagent layer and another reagent layer arranged on the support;

(3) an element comprising a spreading layer and two or more reagent layers arranged on the support;

(4) an element comprising a spreading layer, two or more reagent layers and a water-absorbing layer arranged in order on the support;

(5) an element comprising a spreading layer, a reflection layer (or filtration layer), and two or more reagent layers arranged in order on the support; and (6) an element comprising a spreading layer, a filtration layer, two or more reagent layers, and a water-absorbing layer arranged in order on the support.

In the analytical element of the present invention, at least one reagent layer contains an oxidized nicotinamide coenzyme. The oxidized nicotinamide coenzyme means NAD+ (oxidized nicotinamide adenine dinucleotide) or NADP+ (oxidized nicotinamide adenine dinucleotide phosphate). Use of any of NAD+ and NADP+ can be determined according to the kind of an oxidation-reduction enzyme used as an analyte or a reagent participating in the reaction.

The dry analytical element of the invention contains an electron transmitter compound (i.e., electron carrier) in at least one reagent layer.

The electron transmitter compound serves for receiving an electron from a reduced nicotinamide coenzyme (i.e. electron donator) produced by the reaction of the analyte and then reducing an electron acceptable dye-forming compound. Examples of the electron transmitter compounds include N-methylphenazine methsulfates such as 5-methylphenazinium methylsulfate and 1-mthoxy-5-methylphenazinium methylsulfate and diaphorase (dihydrolipoamide reductase, EC 1.6.4.3.).

The dry analytical element of the invention further contains an electron acceptable dye-forming compound as one of the reagent components.

The electron acceptable dye-forming compound is reduced by the electron transmitter compound to form a compound (i.e., dye) which is photometrically detectable in the visible ray region. The electron acceptable dye-forming compound preferably employed in the invention is a tetrazolium salt. Examples of the tetrazolium salts include 3,3'-(3,3'-dimethoxy-4,4'-biphenylene)-bis(2-(p-nitrophenyl)- 2H-tetrazolium chloride) (=NBT); 3-(p-indophenyl)-2-(p-nitrophenyl)-5-phenyl-2H-tetrazolium chloride (=INT); 3-(4,5-dimethyl-2-thiazolyl)-2H-tetrazolium bromide (=MTT); 3,3'-(4,4'-biphenylene)-bis(2,5-diphenyl-2H-tetrazolium chloride); 3,3'-(3,3'-dimethoxy-4,4'-biphenylene)-bis(2,5-diphenyl-2H-tetrazolium chloride); and 3,3'-(3,3'-bis(2,5-bis(p-nitrophenyl)-2H-tetrazolium chloride).

The reaction system in which the oxidized nicotinamide coenzyme, electron transmitter compound and electron acceptable dye-forming compound are involved is stated in more detail in A. L. Babson, et al., Clinica Chimica Acta, 12 (1965), 210–215; R. J. Gay, et al., Clinical Chemistry, 14, No. 8 (1968), 740–753; and R. D. Gapps II, et al., Clinical Chemistry, 12, No. 7 (1966), 406–413.

In the analytical element of the present invention, the oxidation-reduction enzyme for the analyte is incorporated into at least one layer, whereby the concentration or content of an analyte (substance to be assayed) in a liquid sample can be determined. The analytical element of the invention can be used for measurement of concentration or content of any analyte, provided that the analyte reacts with the oxidation-reduction enzyme (dehydrogenase) and the oxidized nicotinamide coenzyme can serve as an electron acceptor. For example, glycerol dehydrogenase is incorporated in the case of measuring concentration of neutral fat such as glycerol, and lactate dehydrogenase is incorporated in the case of measuring concentration of lactate (or lactic acid).

The reaction system employed in the dry analytical element of the invention can be also used in the determination of activities of various oxidation-reduction enzymes contained in a liquid sample. In more detail, the dry analytical element of the invention can be used to determine activity of any oxidation-reduction enzyme (dehydrogenase) in the case that the oxidized nicotinamide coenzyme serves as an electron acceptor. When the analytical element of the invention is used for determination of activity of an oxidation-reduction enzyme, the reaction system is further incorporated with a substrate of an oxidation reaction (dehydrogenation reaction) in which the oxidation-reduction enzyme acts as a catalyst. For example, lactic acid is further incorporated into the reaction system as a substrate in the case of using the analytical element of the invention for the determination of the lactate dehydrogenase activity. In the case of determining activity of glucose-6-phosphate dehydrogenase, glucose-6-phosphoric acid is further incorporated into the reaction system as a substrate.

The material of the support of the analytical element of the invention preferably is a light-transmissive, water-impermeable support.

Examples of the water-impermeable, light-transmissive supports include transparent supports in the form of a film or a sheet made of a polymer such as polyethylene terephthalate, polycarbonate of bisphenol A, polystyrene and cellulose esters (e.g., cellulose diacetate, cellulose triacetate, cellulose acetate propionate etc.). The thickness of the support generally ranges from approx. 50 μm to approx. 1 mm, preferably from approx. 80 μm to approx. 300 μm.

A hydrophilic polymer can be used for the formation of a water-absorbing layer, a reagent layer, a filtration layer and a light-reflecting layer in the analytical element of the invention. The hydrophilic polymer is a natural or synthetic polymer having a swelling ratio of generally approx. 1.5 to 20, preferably approx. 2.5 to 15, at 30° C. in the case of water absorption.

Examples of the hydrophilic polymers include gelatin (e.g., alkali-treated gelatin, acid-treated gelatin and deionized gelatin), gelatin derivatives (e.g., phthalated gelatin), agarose, polyacrylamide, polyvinyl alcohol and polyvinyl pyrrolidone. If necessary, a surfactant (cationic, amphoteric or nonionic surfactant) may be further added to the hydrophilic polymer.

The light-blocking layer is a water-permeable layer in which light-blocking (or light-reflecting) fine particles are dispersed in a small amount of a film-forming hydrophilic polymer binder. The light-blocking layer may function as light-reflecting layer or background layer as well as blocker to the color of an aqueous liquid spotted on the spreading layer, such as the red of hemoglobin in a whole blood sample, when a detectable change (color change or color development etc.) in the water-absorbing layer is measured from the side of the transparent support through reflection photometry.

Preferred examples of light-blocking and light-reflecting particles are fine titanium dioxide particles and fine barium sulfate particles. In the invention, the light-blocking particles can be incorporated into the spreading layer, if desired.

There may be provided an adhesive layer on the water-absorbing layer or optionally added other layers (e.g., light-blocking layer, filtration layer and reagent layer) to enhance the adhesion of the spreading layer.

The adhesive layer is preferably constituted of a hydrophilic polymer which can bond the spreading layer to other layer to make all of the layers integrated when the polymer is wetted or swelled with water. Examples of the hydrophilic polymer include the polymers employable in the water-absorbing layer. Most preferred are gelatin, gelatin derivatives and polyacrylamide. The dry thickness of the adhesive layer generally ranges from approx. 0.5 μm to approx. 20 μm, preferably from approx. 1 μm to approx. 10 μm.

The adhesive layer may be provided onto other layers as well as the water-absorbing layer. The adhesive layer can be prepared in such a manner that a solution of a hydrophilic polymer and optionally added other agent such as a surfactant is coated on the water-absorbing layer or other layer.

The term "spreading layer" used herein means a layer capable of metering a liquid sample. This function can be said in terms of a layer having a function which is capable of spreading an applied liquid in such a manner that the spread area of the liquid is formed approximately in proportion to the amount of the liquid when the liquid is applied thereon.

The spreading layer can be made of filter paper, nonwoven fabric, woven fabric (e.g., plain woven fabrics such as broadcloth and poplin), knitted fabric (e.g., tricot knitted fabric, double tricot knitted fabric and milanese knitted fabric), glass fiber filter, membrane filter or a three-dimensional lattice structure composed of polymer microbeads as a material constituting a matrix. Preferred are woven fabric and knitted fabric from the viewpoint of preservation of reagents.

When woven fabric or knitted fabric is used as a material of the spreading layer of an integral multilayer analytical element, the fabric is preferably processed to become hydrophilic to enhance the adhesion to an underlying layer. Examples of such process to make the fabric hydrophilic include physical activating process (preferably glow discharge process or corona discharge process) disclosed in Japanese Patent Provisional Publication No. 57(1982)-66359 and hydrophilic polymer permeating process disclosed in Japanese Patent Provisional Publications No. 55(1980)-164356 and No. 57(1982)-66359.

The spreading layer constituted of woven fabric or knitted fabric can be laminated on a water-absorbing layer or an adhesive layer according to the process disclosed in Japanese Patent Provisional Publications No. 55(1980)-164356 and No. 57(1982)-66359. The process is that woven fabric or knitted fabric is laminated under the substantially uniform weak pressure on the wet or swelling buffer layer or adhesive layer which has been still under wet condition after coating or has been supplied with water (or water containing a small amount of a surfactant) after drying.

The spreading layer constituted of a brushed polymer or a membrane filter can be provided according to the process disclosed in Japanese Patent Publication No. 53(1978)-21677, the spreading layer having a three-dimensional lattice structure constituted of polymer microbeads can be provided according to the method disclosed in Japanese Patent Provisional Publication No. 55(1980)-90859, and the reagent sheet or the spreading layer constituted of filter paper or nonwoven fabric can be provided according to the process disclosed in Japanese Patent Provisional Publication No. 57(1982)-148250.

The spreading layer of the analytical element can contain a hydrophilic polymer and/or a surfactant for adjusting its metering property.

Examples of the hydrophlic polymers include cellulose derivatives, polyvinylpyrrolidone, polyvinyl alcohol and polyacrylamide.

As an example of the surfactant, there can be mentioned a nonionic surfactant. Examples of the nonionic surfactants include p-octylphenoxy polyethoxyethanol, p-nonylphenoxy polyethoxyethanol, polyoxyethylene oleyl ether, polyoxyethylene sorbitan monolaulate, p-nonylphenoxy polyglycidol and octyl glucoside.

In the case of using an analyte which hardly permeates an uniformly coated layer of the polymer binder (i.e., case of using a hydrophobic analyte or a high-molecular analyte) such as neutral fat, for instance, glycerol, the porous spreading layer is preferably incorporated with a portion of reagent components, particularly a decomposing enzyme such as lipoprotein lipase.

According to the present invention, an alkali agent or alkaline buffer is incorporated into a layer of the analytical element, which is different from one or more layers containing the oxidized nicotinamide coenzyme and the electron-acceptable dye-forming compound. The alkali agent or alkaline buffer is preferably incorporated into a layer arranged on the layer or layers containing the coenzyme and dye-forming compound, particularly, a porous spreading layer.

Examples of the alkaline buffer or the alkali agent include 2-amino-2-methyl-1,3-propanediol, 2-amino-2-ethyl-1,3-propanediol, diethanolamine, ethanolamine, 2-amino-2-methyl-1-propanediol, tris(hydroxymethyl)aminomethane and trimethylamine. As other examples of the alkali agent or alkaline buffer employable in the invention, there can be mentioned pH buffer agents described, for instance, in "Chemical Handbook, Fundamental Edition", 1312–1320, by Chemical Society of Japan, (Maruzen Tokyo, 1966); "Data for Biochemical Research", Second Edition, 476–508, by R. M. C. Dawson et al., (Oxford at the Clarendom Press, 1969); "Biochemistry", 5, 467-, (1966); and "Analytical Biochemistry", 104, 300–310, (1980).

The layer containing the alkali agent or alkaline buffer is preferably prepared under such condition that the reagent layers of the analytical element shows a pH condition within the range of pH 7.5 to pH 10.0 (particularly, pH 8.0 to 10.0 for an analytical element for quantitative analysis of lactate which utilizes as the dehydrogenase lactate dehydrogenase or for an analytical element for quantitative analysis of neutral fat which utilizes as the dehydrogenase glycerol dehydrogenase or glycerol-3-phosphate dehydrogenase) after when the layer receives a liquid sample containing an analyte.

As mentioned above, the alkali agent or alkaline buffer is preferably incorporated into a porous spreading layer.

The porous spreading layer is preferably incorporated with a hydrophilic polymer and/or a surfactant for the purpose of controlling excessive spreading of a liquid sample introduced into the layer.

Examples of the hydrophilic polymers which can be incorporated into the spreading layer include polyvinyl pyrrolidone, polyvinyl alcohol, polyacrylamide, polyacrylic acid and hydrophilic cellulose derivatives. The hydrophilic cellulose derivatives are cellulose esters produced by etherifying a portion or whole of a hydroxy group with a lower alkyl group having 1–3 carbon atoms or a hydroxy group-substituted lower alkyl group having 1–4 carbon atoms. Examples of the cellulose ethers include water-soluble methyl cellulose, water-soluble ethyl cellulose, water-soluble hydroxyethyl cellulose, water-soluble hydroxypropyl methyl cellulose and water-soluble hydroxybutyl methyl cellulose. Preferred hydrophilic polymers are polyvinyl pyrrolidone, polyvinyl alcohol and water-soluble cellulose esters. These hydrophilic polymers can be employed in combination. The hydrophilic polymer in an amount in the range of about 0.5 to 15 g/m$^2$, preferably about 0.7 to 10 g/m$^2$ can be incorporated into the spreading layer of the analytical element.

The surfactant to be incorporated into the spreading layer can be appropriately selected from nonionic surfactants, cationic surfactants, anionic surfactants and amphoteric surfactants. Preferred is a nonionic surfactant. Examples of the nonionic surfactants include polyhydric alcohol ester ethylene oxide adducts (condensation products), polyethylene glycol monoesters, polyethylene glycol diesters, higher alcohol ethylene oxide adducts (condensation products), alkylphenol ethylene oxide adducts (condensation products) and higher fatty acids. In the invention, two or more these nonionic surfactants can be employed in combination. When the nonionic surfactant is used in combination with the hydrophilic cellulose derivative, preferred is a nonionic surfactant having a HLB value of not less than 10. The nonionic surfactant in an amount in the range of about 0.1 to 3 g/m$^2$, preferably about 0.2 to 2 g/m$^2$ can be incorporated into the spreading layer of the analytical element.

The multilayer analytical element of the present invention can be preferably prepared by a process which comprises the steps of:

forming on said support a reagent layer containing at least said oxidized nicotinamide coenzyme and electron acceptable dye-forming compound dispersed in a hydrophilic polymer;

forming a liquid spreading layer having metering effect;

coating a solution or dispersion containing at least said alkali agent or alkaline buffer in an organic solvent substantially not causing swelling of the hydrophilic polymer in the underlying reagent layer over the spreading layer; and drying the coated layers.

Alternatively, the multilayer analytical element of the present invention can be preferably prepared by a process which comprises the steps of:

forming on said support a reagent layer containing at least said oxidized nicotinamide coenzyme and electron acceptable dye-forming compound dispersed in a hydrophilic polymer;

coating a solution or dispersion containing at least said alkali agent or alkaline buffer in an organic solvent substantially not causing swelling of the hydrophilic polymer in the underlying reagent layer over the underlying reagent layer; and drying the coated layers.

There is no specific limitation on the organic solvent employable in the process, so long as the solvent satisfies the above-mentioned conditions, but preferably used is a polar solvent having a boiling point of not higher than 100° C. Examples of such polar solvents include lower fatty alcohols (e.g., methanol, ethanol, propanol, butanol and isopropyl alcohol), dialkyl ketones (e.g., acetone), dialkylethers (e.g., dimethyl ether), and fatty cyclic ethers (e.g., tetrahydrofuran and dioxane). Preferred is a fatty alcohol. From the viewpoints of working environment, etc., particularly preferred are alcohols having less toxicity to a human body such as ethanol, propanol, butanol and isopropyl alcohol. The concentration of the solution or dispersion is desired to be as high as possible, provided that the solution or dispersion easily contains its contents and homogeneously permeates the porous spreading layer. Although the concentration of the solution or dispersion depends upon the kinds of the puruvate and other optionally incorporatable components such as a pH buffer agent and a hydrophilic polymer, the concentration thereof is generally in the range of approx. 0.2 to 10% preferably in the range of approx. 0.3 to 7%. The solution or dispersion can be prepared according to a known method. The organic solvent may contain water, provided that the incorporation of water does not substantially bring about migration of reagent composition of the underlying layer into the upper layer.

If the spreading layer is incorporated with an alkaline buffer or alkali agent and a surfactant, the surfactant may be incorporated into the layer in the form of a mixture solution containing both of the alkaline buffer or alkali agent (and a hydrophilic polymer, if desired) and the surfactant or in the form of a different solution.

Incorporation of the alkali agent or alkaline buffer into the porous spreading layer is preferably done after laminating the spreading layer on the underlying reagent layer. When the spreading layer is composed of a micro filter, a knitted fabric or a woven fabric, the alkali agent can be incorporated into the spreading layer before laminating the layer. In this case, however, it is difficult to control the content of the alkali agent or alkaline buffer in the porous spreading layer. Accordingly, it is advantageous to incorporate the alkali agent or alkaline buffer into the spreading layer after providing the spreading layer on the previously formed reagent layer (directly or indirectly via an adhesive layer), from the viewpoints of analytical accuracy and manufacturing cost. The alkali agent or alkaline buffert can be incorporated into the spreading layer, for example, by uniformly coating or spraying the agent on the surface of the spreading layer according to a known method. The coated or sprayed buffer agent can be dried by air or under reduced pressure.

It is preferred from the viewpoint of manufacture, packaging, transportation, preservation and measuring operation that an integrated multilayer analytical element of the present invention is cut into pieces of about 15 to 30 mm square or a circle of about 15 to 30 mm in diameter and put in a slide frame to provide an analytical slide as disclosed in Japanese Patent Provisional Publication Nos. 57(1982)-63452 and 54(1979)-156079, Japanese Utility Model Provisional Publication Nos. 56(1981)-142454 and 58(1983)-32350 and Japanese Patent Provisional Publication No. 58(1983)-501144.

About 5 to about 30 μl, preferably about 8 to about 15 μl of an aqueous liquid sample is deposited (spotted) on the porous spreading layer of the analytical element, and, if necessary, the analytical element is incubated at a substantially constant temperature of about 20° to 45° C. A detectable change such as color change or color formation in the element is measured (from the side of the light-transmissive support) by reflection photometry to thereby analyze the analyte in the liquid sample by colorimetry.

Examples of the present invention and comparison examples are given below.

EXAMPLE 1

A coating solution for a reagent layer having the following composition was prepared. In the coating solution was dropped a 1N-sodium hydroxide solution to adjust the coating solution to show pH 6.8. On a surface of a transparent polyethylene terephthalate (PET) film (support) of 180 μm thick having been undercoated with gelatin was coated the coating solution, and the coated layer was dried to form a color-forming reagent layer for detecting neutral fat on the support.

Composition of Coating Solution for Reagent Layer

Alkali-treated gelatin: 17 g/m$^2$
Nonylphenoxypolyethoxyethanol (average oxyethylene unit content: 15) 75 mg/m$^2$
ATP: 1.5 g/m$^2$
Magnesium sulfate: 1.2 g/m$^2$
NAD: 280 mg/m$^2$
3,3'-(3,3'-Dimethoxy-4,4'-biphenylene)bis[2-(p-nitrophenyl)-2H-tetrazolium]dichloride: 550 mg/m$^2$
Sodium citrate: 3.7 g/m$^2$
Diaphorase (EC 1.6.4.3): 6,000 U/m$^2$
Glycerol kinase (EC 2.7.1.30): 1,800 U/m$^2$
Glycerol-3-phosphate dehydrogenase (EC 1.1.99.5): 10,000 U/m$^2$ On the surface of the obtained reagent layer was coated a coating solution having the following composition, to form a light-blocking layer on the reagent layer.

Composition of Coating Solution for Light-blocking Layer

Alkali-treated gelatin: 5.0 g/m$^2$
Rutile titanium dioxide: 28 g/m$^2$
Nonylphenoxy polyethoxyethanol (average oxyethylene unit content: 15): 100 mg/m$^2$ On the surface of the obtained light-blocking layer was coated a coating solution having the following composition, to form an adhesive layer on the light-blocking layer.

Composition of Coating Solution for Adhesive Layer

Alkali-treated gelatin: 2.7 g/m$^2$
Nonylphenoxy polyethoxyethanol (average oxyethylene unit content: 15): 270 mg/m$^2$ Independently, a knitted fabric (average thickness: 250 μm) composed of polyethylene terephthalate spinning yarn (50 deniers) was subjected to a glow discharge treatment to make it hydrophilic. Subsequently, the surface of the adhesive layer was wetted with water in an amount of 30 g/m$^2$ to swell, and then provided thereon the knitted fabric having been treated as above by a pressure laminating method, to form a spreading layer on the adhesive layer.

On the surface of the spreading layer was coated an ethanol dispersion of alkali agent having the following composition in an amount of 200 ml/m$^2$, to form a layer of the ethanol dispersion containing alkali agent on the spreading layer.

Composition of Ethanol Dispersion of Alkali Agent

Ethanol: 500 ml
Polyvinyl pyrrolidone (mean molecular weight: 360,000): 20 g/m$^2$
Nonylphenoxy polyethoxyethanol (average oxyethylene unit content: 40): 5 g/m$^2$
2-Amino-1-methyl-1,3-propanediol: 9 g/m$^2$ The resulting multilayer sheet was then dried to prepare an integral multilayer analytical element for quantitative determination of neutral fat according to the present invention.

Comparison Example 1

The procedure of Example 1 was repeated except for not using an aqueous solution of alkali agent but using water in the same amount instead of ethanol, to prepare an analytical element for comparison.

Comparison Example 2

The procedure of Example 1 was repeated except for not incorporating 2-amino-2-methyl-1,3-propanediol into the ethanol dispersion of alkali agent, to prepare an analytical element for comparison.

Each of the analytical elements obtained in the above examples was cut into a square tip (1.5 mm × 1.5 mm), and each of the tips was placed on a plastic mount disclosed in Japanese Patent Provisional Publication No. 57(1982)-63452, to produce a chemical analytical slide for quantitative determination of neutral fat according to the invention and chemical analytical slides for quantitative determination of neutral fat for comparison.

Each of the three kinds of slides were allowed to stand for one week at temperatures of −25° C. and +45° C. under dry condition, and thereafter each of the slides was spotted with 10 μl of various human serums having different concentrations of neutral fat and incubated at 37° C. for 6 minutes. Then, each of the slides was measured on the reflection optical density from the PET support side at a light of 540 nm (central wavelength).

Separately, the above-described serums were determined on their concentrations of neutral fat according to a glycerol-3-phosphate oxidase method, and a calibration curve was produced based on the determined concentrations of neutral fat to compare those of the comparison examples.

The measurement of optical density of the slide in the case that the concentration of neutral fat was 0 was done by spotting a 7% human albumin solution on the slide.

The results are set forth in Table 1.

TABLE 1

| Concentration of Neutral Fat (mg/dl) | Example 1 (−25° C./ 45° C.) | Com. Ex. 1 (−25° C./ 45° C.) | Com. Ex. 2 (−25° C./ 45° C.) |
| --- | --- | --- | --- |
| 0 | 0.178/0.180 | 0.295/0.503 | 0.326/0.515 |
| 65 | 0.305/0.307 | 0.411/0.603 | 0.438/0.520 |
| 381 | 0.835/0.850 | 0.962/1.030 | 0.991/0.940 |
| 525 | 1.045/1.061 | 1.102/1.081 | 1.112/0.932 |

In the integral multilayer analytical element for quantitative determination of neutral fat according to the invention, increase of the optical density as the background coloring was very small even after the element was allowed to stand for one week at 45° C. Further, the optical density hardly decreased in the wide range with respect to the amount of the neutral fat (i.e., range up to approx. 3.3 times as much as the upper limit of its normal value), and a calibration curve having a steep inclination was obtained. Hence, it was confirmed that the analytical element of the invention had a high accuracy for quantitative determination.

EXAMPLE 2

On a surface of a colorless transparent polyethylene terephthalate (PET) film (support) of 180 μm thick having been undercoated with gelatin was coated the following composition in the form of an aqueous solution, and the coated layer was dried to form a color-forming reagent layer for detection of lactate.

Composition of Color-Forming Reagent Layer

Alkali-treated gelatin: 10 g/m²
Nonylphenoxy polyglycidyl ether (average glycidyl unit content: 10): 200 mg/m²
Lactate dehydrogenase (EC 1.1.1.27, origin: pig heart): 12,000 U/m²
Diaphorase (EC 1.6.4.3, origin: microorganism): 5,600 U/m²
NAD+: 600 mg/m²
3,3′-(3,3′-Dimethoxy-4,4′-biphenylene)bis[2-(p-nitrophenyl)-2H-tetrazolium] dichloride: 400 mg/m²
Sodium citrate: 6.0 g/m²

Independently, a knitted fabric (average thickness: 250 μm) composed of polyethylene terephthalate spinning yarn (50 deniers) was subjected to a glow discharge treatment to make it hydrophilic. Subsequently, the surface of the reagent layer was wetted with water in an amount of 30 g/m² to swell, and then provided thereon the knitted fabric having been treated as above by a pressure laminating method, to form a spreading layer on the adhesive layer.

On the surface of the spreading layer was coated an ethanol solution having the following composition in an amount of 200 ml/m², to form a layer of the ethanol solution containing alkali agent on the spreading layer.

Composition of Ethanol Dispersion of Alkali Agent

Ethyl alcohol: 500 ml
Nonylphenoxy polyethoxyethanol (average oxyethylene unit content: 9–10): 5 g
2-Amino-1-methyl-1,3-propanediol: 9 g
Polyvinyl pyrrolidone (mean molecular weight: 360,000): 16 g/m²

The resulting multilayer sheet was then dried to prepare an integral multilayer analytical element for quantitative determination of lactate.

The analytical element was cut into square tips (1.5 mm × 1.5 mm), and each of the tips was placed on a plastic mount disclosed in Japanese Patent Provisional Publication No. 57(1982)-63452, to produce a chemical analytical slide for quantitative determination of lactate.

Each of the slides was spotted with 10 μl of various aqueous lactate solution having different concentrations of lactate (0, 1, 5, 10, 15 and 20 mg/dl, and incubated at 37° C. for 6 minutes. Then, each of the slides was measured on the reflection optical density from the PET support side at light of 540 nm (central wavelength) to prepare a calibration curve. The obtained calibration curve is numerically set out in Table 2.

TABLE 2

| | Amount of Lactate (mg/dl) | | | | | |
| --- | --- | --- | --- | --- | --- | --- |
| | 0 | 1 | 5 | 10 | 15 | 20 |
| OD | 0.164 | 0.190 | 0.351 | 0.532 | 0.689 | 0.713 |

EXAMPLE 3

The same slide as prepared in Example 2 was tested for determination of interference by bilirubin.

A solution having the composition set forth in Table 3 was prepared using OMEGA Chemistry Control Serum Elevated Bilirubin (measured value of bilirubin content: 30 mg/dl) and a control serum (measured value of lactate (expressed as lactic acid): 8 mg/dl). This solution was applied on the slide and processed in the same manner as in Example 2, for evaluating influence of bilirubin.

The results are set forth in Table 3.

TABLE 3

| | Content of Solution (Volume part) | | |
| --- | --- | --- | --- |
| | No. 1 | No. 2 | No. 3 |
| Serum | 0.5 | 0.5 | 0.5 |
| Bilirubin Solution | 0 | 0.2 | 0.5 |
| Water | 0.5 | 0.3 | 0 |
| Optical Density | 0.310 | 0.312 | 0.309 |

Remark: Standard value was a reflection optical density obtained by the measurement of a slide using the bilirubin solution or a sample solution containing no hemoglobin.

The results set forth in Table 3 indicate that the analytical element of the invention is employable for quantitative analysis of lactate at a content of 4 mg/dl (lower limit of normal value) substantially free from error (error: within ±0.65%) caused by the presence of bilirubin in a wide range of from absence of bilirubin to 15 mg/dl (abnormally high bilirubin content corresponding to a value of 15 times as much as a normal value).

EXAMPLE 4

The same slide as prepared in Example 2 was tested for determination of interference by hemoglobin.

A solution having the composition set forth in Table 4 was prepared using a control serum (measured value of hemoglobin content: 1,400 mg/dl) and another control serum (measured value of lactate (expressed as lactic acid): 8 mg/dl). This solution was applied on the slide and processed in the same manner as in Example 2, for evaluating influence of hemoglobin.

The results are set forth in Table 4.

TABLE 4

|  | Content of Solution (Volume part) | | |
|---|---|---|---|
|  | No. 1 | No. 2 | No. 3 |
| Serum | 0.5 | 0.5 | 0.5 |
| Hemoglobin Solution | 0 | 0.2 | 0.5 |
| Water | 0.5 | 0.3 | 0 |
| Optical Density | 0.315 | 0.310 | 0.309 |

The results set forth in Table 4 indicate that the analytical element of the invention is employable for quantitative analysis of lactate at a content of 4 mg/dl (lower limit of normal value) substantially free from error (error: within ±1.90%) caused by the presence of hemoglobin in a wide range of from absence of hemoglobin to 15 mg/dl (abnormally high hemoglobin content corresponding to that of homolyzed whole blood, hemolyzed plasma, or hemolyzed serum).

EXAMPLE 5

The same slide as prepared in Example 2 was kept for 4 weeks in a sealed dark vessel inside of which was maintained at 30° C. and dried by the presence of silica gel to determine a background coloring (fog) by reflection photometry.

The results are set forth in Table 5.

Comparison Example 3

The same slide was prepared in the same manner as in Example 2 except that the alkali agent was incorporated into the underlying reagent layer in place of the spreading layer. The obtained slide was kept for 4 weeks in a sealed dark vessel inside of which was maintained at 30° C. and dried by the presence of silica gel to determine a background coloring (fog) by reflection photometry.

The results are set forth in Table 5.

TABLE 5

|  | Period of Storage | | | |
|---|---|---|---|---|
|  | 0 Day | 5 Days | 2 Weeks | 4 Weeks |
| Example 5 | 0.165 | 0.168 | 0.170 | 0.169 |
| Com. Ex. 3 | 0.178 | 0.423 | 0.529 | 0.662 |

The results set forth in Table 5 indicate that the analytical element of the invention containing the alkali agent in the spreading layer is more stable and more reduced in the formation of fog than the analytical element for comparison containing the alkali agent in the reagent layer in combination with other color-forming reagents.

EXAMPLE 6

A coating solution for a reagent layer having the following composition was prepared. On a surface of a transparent polyethylene terephthalate (PET) film (support) of 180 μm thick having been undercoated with gelatin was coated the coating solution, and the coated layer was dried to form a color-forming reagent layer for detecting neutral fat on the support.

Composition of Coating Solution for Reagent Layer

Alkali-treated gelatin: 22 g/m$^2$
Nonylphenoxypolyethoxyethanol (average oxyethylene unit content: 15), 100 mg/m$^2$
ATP: 1.9 g/m$^2$
Magnesium sulfate: 1.6 g/m$^2$
NAD: 360 mg/m$^2$
3,3'-(3,3'-Dimethoxy-4,4'-biphenylene)bis[2-(p-nitrophenyl)-2H-tetrazolium] dichloride: 720 mg/m$^2$
Diaphorase (EC 1.6.4.3): 7,700 U/m$^2$
Glycerol kinase (EC 2.7.1.30): 2,500 U/m$^2$
Glycerol-3-phosphate dehydrogenase (EC 1.1.99.5): 15,000 U/m$^2$ On the surface of the obtained reagent layer was coated a coating solution having the following composition, to form a light-blocking layer on the reagent layer.

Composition of Coating Solution for Light-blocking Layer

Alkali-treated gelatin: 3.2 g/m$^2$
Rutile titanium dioxide: 28 g/m$^2$
Nonylphenoxy polyethoxyethanol (average oxyethylene unit content: 15): 100 mg/m$^2$ On the surface of the obtained light-blocking layer was coated a coating solution having the following composition, to form an adhesive layer on the light-blocking layer.

Composition of Coating Solution for Adhesive Layer

Alkali-treated gelatin: 2.7 g/m$^2$
Nonylphenoxy polyethoxyethanol (average oxyethylene unit content: 15): 200 mg/m$^2$ Independently, a knitted fabric (average thickness: 250 μm) composed of polyethylene terephthalate spinning yarn (50 deniers) was subjected to a glow discharge treatment to make it hydrophilic. Subsequently, the surface of the adhesive layer was wetted with water in an amount of 30 g/m$^2$ to swell, and then provided thereon the knitted fabric having been treated as above by a pressure laminating method, to form a spreading layer on the adhesive layer.

On the surface of the spreading layer was coated an ethanol dispersion of alkali agent having the following composition in an amount of 200 ml/m$^2$, to form a layer of the ethanol dispersion containing alkali agent on the spreading layer.

Composition of Ethanol Dispersion of Alkali Agent

Ethanol: 500 ml
Polyvinyl pyrrolidone (mean molecular weight: 360,000): 20 g/m$^2$
Nonylphenoxy polyethoxyethanol (average content of oxyethylene: 40): 5 g/m$^2$
2-Amino-1-methyl-1,3-propanediol: 9 g/m$^2$
(to the composition was added a solution of 11,400 U of lipoprotein lipase in 5 ml of water).

The resulting multilayer sheet was then dried to prepare an integral multilayer analytical element for quantitative determination of neutral fat according to the present invention.

Comparison Example 4

The procedure of Example 6 was repeated except for not using an aqueous solution of alkali agent but using water in the same amount instead of ethanol, to prepare an analytical element for comparison.

Comparison Example 5

The procedure of Example 6 was repeated except for incorporating 2-amino-2-methyl-1,3-propanediol (3.6 g/m$^2$) and lipoprotein lipase (4,500 U/m$^2$) into the adhesive layer in place of the spreading layer, to prepare an analytical element for comparison.

Each of the analytical elements obtained in the above examples was cut into a square tip (1.5 mm×1.5 mm), and each of the tips was placed on a plastic mount, to produce a chemical analytical slide for quantitative determination of neutral fat according to the invention and chemical analytical slides for quantitative determination of neutral fat for comparison.

Each of the three kinds of slides were allowed to stand for one week at temperatures of −25° C. and +45° C. under dry condition, and thereafter each of the slides was spotted with 10 μl of various human serums having different concentrations of neutral fat and incubated at 37° C. for 6 minutes. Then, each of the slides was measured on the reflection optical density from the PET support side at a light of 540 nm (central wavelength).

Separately, the above-described serums were determined on their concentrations of neutral fat according to a glycerol-3-phosphate oxidase method, and a calibration curve was produced based on the determined concentrations of neutral fat to compare those of the comparison examples.

The measurement of optical density of the slide in the case that the concentration of neutral fat was 0 was done by spotting a 7% human albumin solution on the slide.

The results are set forth in Table 6.

TABLE 6

| Concentration of Neutral Fat (mg/dl) | Example 6 (−25° C./ 45° C.) | Com. Ex. 4 (−25° C./ 45° C.) | Com. Ex. 5 (−25° C./ 45° C.) |
| --- | --- | --- | --- |
| 0 | 0.178/0.180 | 0.241/0.540 | 0.241/0.602 |
| 62 | 0.306/0.314 | 0.379/0.573 | 0.261/0.618 |
| 167 | 0.545/0.547 | 0.560/0.625 | 0.323/0.641 |
| 238 | 0.625/0.629 | 0.681/0.653 | 0.357/0.655 |
| 383 | 0.829/0.836 | 0.873/0.718 | 0.408/0.683 |
| 527 | 1.049/1.048 | 1.064/0.773 | 0.459/0.705 |

In the integral multilayer analytical element for quantitative determination of neutral fat according to the invention, increase of the optical density as the background coloring was very small even after the element was allowed to stand for one week at 45° C. Further, the optical density hardly decreased in the wide range with respect to the amount of the neutral fat (i.e., range up to approx. 3.3 times as much as the upper limit of its normal value), and a calibration curve having a steep inclination was obtained. Hence, it was confirmed that the analytical element of the invention had a high accuracy for quantitative determination.

EXAMPLE 7

The same slide as in Example 6 for quantitative determination of neutral fat was prepared.

Each of the slides was spotted with 10 μl of various human whole blood (collected in the presence of heparin) solution having different concentrations of neutral fat (0, 62, 167, 238, 383 and 527 mg/dl, and incubated at 37° C. for 6 minutes. Then, each of the slides was measured on the reflection optical density from the PET support side at light of 540 nm (central wavelength) to prepare a calibration curve. The obtained calibration curve is numerically set out in Table 7.

TABLE 7

| | Amount of Neutral Fat (mg/dl) | | | | | |
| --- | --- | --- | --- | --- | --- | --- |
| | 0 | 62 | 167 | 238 | 383 | 527 |
| OD | 0.178 | 0.306 | 0.545 | 0.625 | 0.829 | 1.049 |

The results set forth in Table 7 indicate that the analytical element of the invention gives a steep calibration and therefore gives analytical results with high accuracy.

EXAMPLE 8

The same slide as prepared in Example 6 was tested for determination of interference by bilirubin.

Three kinds of solutions having the composition set forth in Table 3 was prepared using OMEGA Chemistry Control Serum Elevated Bilirubin (measured value of bilirubin content: 30 mg/dl), a serum containing neutral fat (measured value of neutral fat: 690 mg/dl), and a physiological saline solution. These solution were applied on the slide and processed in the same manner as in Example 7, for evaluating influence of bilirubin.

The results are set forth in Table 8.

TABLE 8

| | Content of Solution (Volume part) | | |
| --- | --- | --- | --- |
| | No. 1 | No. 2 | No. 3 |
| Serum | 0.5 | 0.5 | 0.5 |
| Control serum | 0 | 0.2 | 0.5 |
| Saline Solution | 0.5 | 0.3 | 0 |
| Neutral Fat (Analyte) | 345 | 345 | 345 |
| Bilirubin (Interfering substance) | 0 | 6.0 | 15 |
| Optical Density | 0.812 | 0.810 | 0.817 |

The results set forth in Table 8 indicate that the analytical element of the invention is employable for quantitative analysis of neutral fat at a content of 345 mg/dl (a value of approx. twice as much as normal value) substantially free from error (error: within ±0.62%) caused by the presence of bilirubin in a wide range of from absence of bilirubin to 15 mg/dl (abnormally high bilirubin content corresponding to a value of 15 times as much as a normal value).

EXAMPLE 9

The same slide as prepared in Example 6 was tested for determination of interference by hemoglobin.

Three kind of solutions having the composition set forth in Table 9 were prepared using a control serum (measured value of hemoglobin content: 1,000 mg/dl), and a serum (measured value of neutral fat: 690 mg/dl) and a physiological saline solution. This solution was applied on the slide and processed in the same manner as in Example 6, for evaluating influence of hemoglobin.

The results are set forth in Table 9.

TABLE 9

| | Content of Solution (Volume part) | | |
| --- | --- | --- | --- |
| | No. 1 | No. 2 | No. 3 |
| Serum | 0.5 | 0.5 | 0.5 |
| Control serum | 0 | 0.2 | 0.5 |
| Saline Solution | 0.5 | 0.3 | 0 |
| Neutral Fat (Analyte) | 345 | 345 | 345 |
| Bilirubin (Interfering substance) | 0 | 200 | 500 |

TABLE 9-continued

| | Content of Solution (Volume part) | | |
|---|---|---|---|
| | No. 1 | No. 2 | No. 3 |
| Optical Density | 0.820 | 0.814 | 0.817 |

The results set forth in Table 9 indicate that the analytical element of the invention is employable for quantitative analysis of neutral fat at a content of 345 mg/dl (a value of approx. twice as much as normal value) substantially free from error (error: within −0.73%) caused by the presence of hemoglobin in a wide range of from absence of hemoglobin to 500 mg/dl (abnormally high hemoglobin content corresponding to that of homolyzed whole blood, hemolyzed plasma, or hemolyzed serum).

We claim:

1. A process for the preparation of a dry integral multilayer analytical element having reagent layers containing a dehydrogenase, oxidized nicotinamide coenzyme, an electron transport compound, an electron acceptable dye-forming compound, an alkali agent or an alkaline buffer selected from the group consisting of 2-amino-2-methyl-1,3-propanediol, 2-amino-2-ethyl-1,3-propanediol, diethanolamine, ethanolamine, 2-amino-2-methyl-1-propanediol, tris(hydroxymethyl)aminomethane and trimethylamine provided on a light-transmissive, water-impermeable support which comprises the steps of:
   forming on said support a reagent layer containing at least said oxidized nicotinamide coenzyme and electron acceptable dye-forming compound dispersed in a hydrophilic polymer;
   forming a spreading layer having a metering effect;
   coating a solution or dispersion containing at least said alkali agent or alkaline buffer in an organic solvent which causes substantially no swelling of the hydrophilic polymer in the underlying reagent layer over the spreading layer; and
   drying the coated layers.

2. A process for the preparation of a dry integral multilayer analytical element having reagent layers containing a dehydrogenase, oxidized nicotinamide coenzyme, an electron transport compound, an electron acceptable dye-forming compound and an alkali agent or alkaline buffer selected from the group consisting of 2-amino-2-methyl-1,3-propanediol, 2-amino-2-ethyl-1,3-propanediol, diethanolamine, ethanolamine, 2-amino-2-methyl-1-propanediol, tris(hydroxymethyl)aminomethane and trimethylamine provided on a light-transmissive, water-impermeable support which comprises the steps of:
   forming on said support a reagent layer containing at least said oxidized nicotinamide coenzyme and electron acceptable dye-forming compound dispersed in a hydrophilic polymer;
   coating a solution or dispersion containing at least said alkali agent or alkaline buffer in an organic solvent which causes substantially no swelling of the hydrophilic polymer in the underlying reagent layer over the underlying reagent layer; and
   drying the coated layers.

3. The process as defined in claim 1 wherein said hydrophilic polymer is selected from the group consisting of gelatin, hydrophilic gelatin derivative, agarose, polyacrylamide, polyvinyl alcohol and polyvinyl pyrrolidone.

4. The process as defined in claim 1 wherein said organic solvent is selected from the group consisting of alcohols, dialkyl ketones, dialkylethers and cyclic ethers.

5. The process as defined in claim 1 wherein said organic solvent is selected from the group consisting of methanol, ethanol, propanol, butanol, isopropyl alcohol, acetone, dimethylether, tetrahydrofuran and dioxane.

6. The process as defined in claim 2 wherein said hydrophilic polymer is selected from the group consisting of gelatin, hydrophilic gelatin derivative, agarose, polyacrylamide, polyvinyl alcohol and polyvinyl pyrrolidone.

7. The process as defined in claim 2 wherein said organic solvent is selected from the group consisting of alcohols, dialkyl ketones, dialkylethers and cyclic ethers.

8. The process as defined in claim 2 wherein said organic solvent is selected from the group consisting of methanol, ethanol, propanol, butanol, isopropyl alcohol, acetone, dimethyl ether, tetrahydrofuran and dioxane.

* * * * *